(12) United States Patent
Vogt et al.

(10) Patent No.: US 9,010,586 B2
(45) Date of Patent: Apr. 21, 2015

(54) CARTRIDGE WITH LOCKABLE FEED PLUNGER

(75) Inventors: Sebastian Vogt, Erfurt (DE); Tim Schnieber, Frankfurt (DE)

(73) Assignee: Heraeus Medical GmbH, Wehrheim (DE)

( * ) Notice: Subject to any disclaimer, the term of this patent is extended or adjusted under 35 U.S.C. 154(b) by 199 days.

(21) Appl. No.: 13/291,595

(22) Filed: Nov. 8, 2011

(65) Prior Publication Data

US 2012/0132675 A1 May 31, 2012

(30) Foreign Application Priority Data

Nov. 25, 2010 (DE) .......................... 10 2010 052 323

(51) Int. Cl.
*B65D 88/54* (2006.01)
*B67D 7/60* (2010.01)
*B01F 13/06* (2006.01)
*B01F 15/00* (2006.01)
*A61B 17/88* (2006.01)
*B01F 11/00* (2006.01)
*B01F 13/00* (2006.01)

(52) U.S. Cl.
CPC .......... *A61B 17/8825* (2013.01); *B01F 11/0054* (2013.01); *B01F 13/002* (2013.01)

(58) Field of Classification Search
USPC ........... 222/327, 386, 386.5, 325, 326, 145.1, 222/328; 366/190, 195, 139, 163.1, 189, 366/602, 183.1, 183.2, 183.3, 183.4; 604/199
See application file for complete search history.

(56) References Cited

U.S. PATENT DOCUMENTS

| 2,855,130 | A | * | 10/1958 | Hosler | 222/386.5 |
| 3,319,841 | A | * | 5/1967 | Berg | 222/386.5 |
| 3,752,367 | A | * | 8/1973 | Sundholm | 222/256 |
| 4,027,810 | A | * | 6/1977 | vanManen | 222/327 |
| 4,671,263 | A | | 6/1987 | Draenert | |

(Continued)

FOREIGN PATENT DOCUMENTS

DE 3640279 A1 11/1986
DE 43 02 230 A1 8/1993

(Continued)

OTHER PUBLICATIONS

S.J Breusch et al. "Current Status of Cemented Total Hip Arthroplasty in Germany" Z Orthop Ihre Grenzgeb 1999; 137(2): 101-107 (Abstract in English).

(Continued)

*Primary Examiner* — Kevin P Shaver
*Assistant Examiner* — Stephanie E Williams
(74) *Attorney, Agent, or Firm* — Norris McLaughlin & Marcus, P.A.

(57) ABSTRACT

A cartridge for squeezing-out a cartridge content, like a cement, or a medical cement, having a cylindrical hollow space bordered by a cartridge wall, a feed plunger arranged in the hollow space to be mobile along the cylinder axis of the hollow space and abutting the cartridge wall, and at least one snap-in means for locking the feed plunger in place at the cartridge wall, to a locking device arranged on the feed plunger and comprises at least a snap-in means which is accessible from outside when the feed plunger is locked. The invention also provides a cartridge system with a cartridge for squeezing out content and a method for dispensing such cartridge content, preferably a cement, through the use of a cartridge of said type.

30 Claims, 4 Drawing Sheets

(56) References Cited

U.S. PATENT DOCUMENTS

Figure 1:
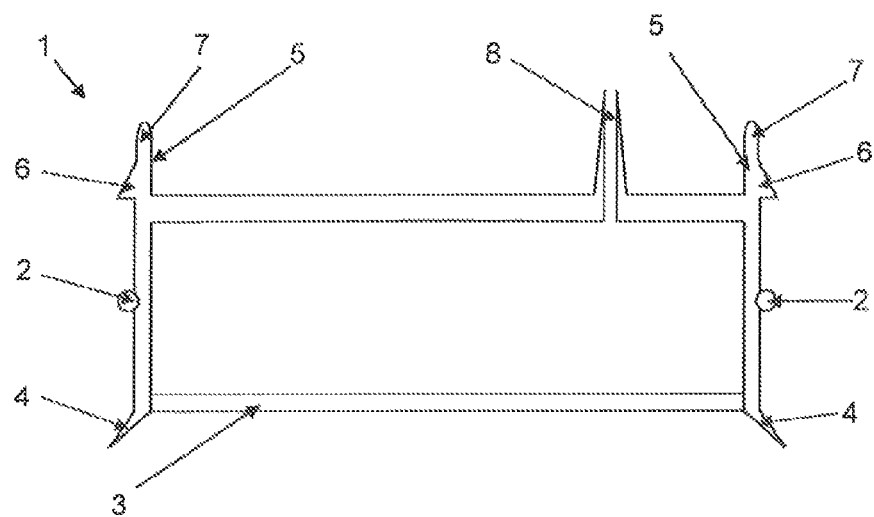

| | | | |
|---|---|---|---|
| 4,973,168 | A | 11/1990 | Chan |
| 5,100,214 | A | 3/1992 | Kitaue |
| 5,344,232 | A | 9/1994 | Nelson et al. |
| 5,586,821 | A | 12/1996 | Bonitati et al. |
| 5,588,745 | A | 12/1996 | Tanaka et al. |
| 5,624,184 | A | 4/1997 | Chan |
| 5,997,544 | A | 12/1999 | Nies et al. |
| 6,033,105 | A | 3/2000 | Barker et al. |
| 6,709,149 | B1 | 3/2004 | Tepic |
| 6,755,563 | B2 | 6/2004 | Wahlig et al. |
| 7,938,572 | B2 * | 5/2011 | Lidgren et al. ............ 366/108 |
| 8,235,255 | B2 * | 8/2012 | Springhorn et al. ......... 222/386 |
| 8,361,078 | B2 * | 1/2013 | Beyar et al. ............... 606/94 |
| 2002/0118596 | A1 | 8/2002 | Mizutani et al. |
| 2005/0128867 | A1 | 6/2005 | Henniges et al. |
| 2005/0211732 | A1 * | 9/2005 | Cable ........................ 222/327 |
| 2011/0114212 | A1 | 5/2011 | Greter et al. |

FOREIGN PATENT DOCUMENTS

| | | |
|---|---|---|
| DE | 10 2009 031 178 | 9/2010 |
| EP | 0 6920229 A1 | 7/1995 |
| EP | 1 020 167 A2 | 1/2000 |
| EP | 1 005 901 A2 | 6/2000 |
| EP | 1 016 452 A2 | 7/2007 |
| EP | 2 008 707 A1 | 12/2008 |
| SE | WO 94/26403 | 11/1994 |
| SE | WO 97/18031 | 5/1997 |
| WO | 0185070 A1 | 11/2001 |
| WO | WO 02/102287 A1 | 12/2002 |
| WO | 2010 012114 A1 | 2/2010 |

OTHER PUBLICATIONS

J. Charnley, "Anchorage of the Femoral Head Prosthesis to the Shaft of the Femur" The Journal of Bone and Joint Surgery Feb. 1960; vol. 42 B, No. 1.

Chinese Office Action corresponding to Chinese Application No. 201110382356.2 dated Sep. 18, 2014.

* cited by examiner

CARTRIDGE WITH LOCKABLE FEED PLUNGER

BACKGROUND OF THE INVENTION (1) Field of the Invention

The invention relates to a cartridge for squeezing-out a cartridge content, in particular a cement, particularly preferably a medical cement, comprising at least one cylindrical hollow space bordered by a cartridge wall, at least one feed plunger that is arranged in the hollow space to be mobile along the cylinder axis of the hollow space and abuts on the cartridge wall, and at least one snap-in means that can be used to lock the feed plunger in place at the cartridge wall.

The invention also relates to a cartridge system having a cartridge of this type as well as a method for dispensing cartridge content, preferably a cement, particularly preferably a medical cement, through the use of a cartridge of said type.

(2) Description of Related Art

Bone cements made of polymethylmethacrylate (PMMA) have been known for decades and are based on the ground-breaking work of Sir Charnley (Charnley, J.: Anchorage of the femoral head prosthesis of the shaft of the femur. J. Bone Joint Surg. 42 (1960) 28-30.). The basic structure of PMMA bone cements has remained the same ever since. PMMA bone cements consist of a liquid monomer component and a powder component. The monomer component generally contains the monomer, methylmethacrylate, and an activator (N,N-dimethyl-p-toluidine) dissolved therein. The powder component consists of one or more polymers that are made by polymerisation, preferably suspension polymerisation, based on methylmethacrylate and co-monomers, such as styrene, methylacrylate or similar monomers, a radio-opaquer, and the initiator, dibenzoylperoxide. Mixing the powder component and the monomer component, a dough that can be shaped plastically is generated by swelling of the polymers of the powder component swell in the methylmethacrylate. Mixing the powder component and the monomer component, the activator, N,N-dimethyl-p-toluidine, reacts with dibenzoylperoxide while forming radicals. The radicals thus formed trigger the radical polymerization of the methylmethacrylate. Upon advancing polymerization of the methylmethacrylate, the viscosity of the cement dough increases until the cement dough solidifies.

Polymethylmethacrylate bone cements can be mixed by mixing the cement powder and the monomer liquid in suitable mixing beakers with the aid of spatulas. This procedure is disadvantageous in that air inclusions may be present in the cement dough thus formed and cause destabilization of the bone cement later on. For this reason, it is preferred to mix bone cement powder and monomer liquid in vacuum mixing systems, since mixing in a vacuum removes air inclusions from the cement dough to a large extent and thus achieves optimal cement quality (Breusch S. J. at al.: Der Stand der Zementiertechnik in Deutschland. Z Orthop. 1999, 137: 101-07). Bone cements mixed in a vacuum have clearly reduced porosity and thus show improved mechanical properties in cured condition.

A large number of vacuum cementing systems has been developed of which the following shall be listed for exemplary purposes: DE 36 40 279 A1, EP 1 020 167 A2, EP 1 016 452 A2, EP 1 005 901 A2, U.S. Pat. Nos. 6,033,105 A, 5,624,184 A, 5,588,745 A, 5,586,821 A, 5,344,232 A, 5,100, 241 A, 4,973,168 A, 4,671,263 A, WO 99/67015 A1, WO 94/26403 A1.

A refinement are cementing systems, in which both the cement powder and the monomer liquid are packaged in separate compartments of the mixing systems and are mixed with each other only right before the application of the cement in the cementing system (DE 10 2009 031 178 B3, U.S. Pat. No. 5,997,544 A, EP 0 692 229 A1, U.S. Pat. No. 6,709,149 B1).

In most cementing systems known to date, there is a problem in that, during the mixing, in particular during vacuum mixing of the cement, the feed plunger that can be shifted axially in the cement container needs to be fixed in place, and in that, in contrast, the feed plunger needs to be axially mobile after the mixing in order for the cement dough to be squeezed out due to the axial motion of the feed plunger resulting from the application of pressure on the feed plunger by an applicator gun. Different technical solutions for this problem have been proposed.

EP 0 861 117 A1 discloses a cementing device, in which the feed plunger is secured through a mobile pin that can be pulled out after the cement is mixed such that the plunger thus becomes axially mobile.

DE 43 02 230 A1 describes a cementing device, in which the feed plunger is fixed in place by fins that engages cut-outs in the cartridge floor. Twisting the feed plunger with respect to the cement cartridge twists the fins out of the cut-outs and the feed plunger becomes unlocked.

A totally different fixation of the feed plunger is proposed in WO 02/102287 A1. Here, the feed plunger is connected to the cement container through a breakable connection in such a manner that the feed plunger becomes mobile only by breaking the connection between the feed plunger and the cement container.

EP 2 008 707 A1 describes a closure for a generic cartridge, in which a feed plunger has cut-outs on the outside and a cartridge wall has cut-outs on the inside that are engaged by inside and outside snap-in means of a snap-in ring. The feed plunger is unlocked through the application of an applicator gun and overcoming the snap-in resistance.

This is disadvantageous in that an applicator gun needs to be applied in order to detach the feed plunger. Moreover, the cut-outs are weak sites in the cartridge wall onto which the pressure acts while the cartridge content is being squeezed out, and at which the cartridges might therefore break.

BRIEF SUMMARY OF THE INVENTION

Accordingly, it is the object of the invention to overcome the disadvantages of the prior art. In particular, easy manual unlocking shall be feasible. Moreover, the structure shall become simpler and therefore less expensive. At the same time, high stability of the cartridge must be achieved as well.

Accordingly, a device for dispensing and, if necessary, for mixing of bone cement shall be developed, in which the locking of the feed plunger can be undone easily through manual means without loose parts, such as pins, being released. Moreover, the unlocking shall not require any elements of an outer packaging, such as unlocking through rotating the cement cartridge against the fins of a blister or applying an applicator gun. Moreover, the locking, the feed plunger, and the cartridge as well shall be manufacturable with minimal effort.

The object of the invention is met in that at least one locking device is arranged on the feed plunger and comprises at least one of the snap-in means and which is accessible from outside when the feed plunger is locked.

This ensures that the feed plunger can be unlocked easily, whereby the structure of the locking device can be implemented very simply and thus cost-efficiently as well.

A cylindrical body or a cartridge with a cylindrical hollow space shall be understood to not only mean those with circular footprints, but very generally other cylindrical geometries as well, for example with oval or angular footprints. According to the invention, the internal space of the cartridge can comprise further, non-cylindrical hollow spaces aside from the cylindrical hollow space.

According to the invention, it is particularly advantageous for the feed plunger to abut on the cartridge wall along the entire circumference thereof, preferably abutting tightly, particularly preferably abutting in a pressure-tight manner.

Moreover, the feed plunger can be provided to be locked to the locking.

Moreover, the locking device or locking devices can be provided to comprise all snap-in means.

A dispensing device according to the invention can also provide that each locking device comprises a grasping part, preferably in the form of an extension, and the grasping part or grasping parts projects or project, respectively, at least in regions thereof, from the hollow space, such that the locking device can be unlocked manually and/or is arranged on the inside of a part of the hollow space that is accessible from outside such that each locking device can be unlocked manually from outside through the grasping part or grasping parts.

A refinement of the invention provides the locking device or locking devices to be connected to the feed plunger in a fixed manner or to, preferably, be implemented to be the same part as the feed plunger.

An embodiment that is particularly easy to operate manually results according to the invention if the invention provides two locking devices on the feed plunger, which preferably are arranged to be opposite from each other.

A particularly expedient, advantageous refinement of the invention provides the one or more snap-in means to reach over the cartridge wall and/or into a groove in the cartridge wall.

If a groove is provided in the cartridge wall, the invention can provide that the groove is arranged in a region of the cartridge wall over which the part of the feed plunger abutting on the cartridge wall does not travel while the cartridge is being squeezed out.

Moreover, the feed plunger can be provided to comprise a cylindrical bushing.

In this context, the invention can provide a mixing rod to be arranged in the bushing and to project from the hollow space that can be used to mix a cartridge content in the hollow space, and which preferably comprises a pre-determined breakage site.

This in turn can be provided in that a mixing vane is arranged on the mixing rod inside the cartridge.

A refinement of the invention that is particularly well-suited for medical applications results if the feed plunger comprises a vacuum connection through which gas can be evacuated from the inside of the cartridge.

In this context, the invention can provide at least one semi-permeable wall, in particular a porous disc, that is permeable to gas and impermeable to powder, to be arranged in the gas bushing of the vacuum connection.

For ease of operation of the locking device, the invention can provide that at least one locking device, preferably all locking devices, can be shifted, tipped and/or bent in the direction of the cylinder axis of the hollow space or can be broken off of the feed plunger, preferably through manual means.

An even more easily operated refinement of the invention results if the snap-in elements, at least over regions thereof, project over the edge of the cartridge wall in radial direction with respect to the cylinder axis of the hollow space when the feed plunger is locked.

Moreover, the invention can provide that the hollow space is closed on one side through the feed plunger or is separated into a region on the inside of the cartridge and a region that is accessible from outside.

In order to improve the sealing of the inside of the cartridge, the invention can provide the feed plunger to comprise at least one sealing ring that abuts on the cartridge wall in circumferential direction.

The invention can just as well provide the feed plunger to comprise, below the one or more snap-in means, at least one notch in the feed plunger jacket each in extension of the external sides of the one or more snap-in means.

Moreover, the invention can provide the cartridge to comprise an outlet opening, in particular a dispensing tube for dispensing a cartridge content, on the side that is opposite from the feed plunger in the locked position.

In this context, the invention can provide a fastening means, in particular a thread, preferably an external thread, to be arranged in the region of the outlet opening of the cartridge.

A fastening means or thread of said type can be used to fasten a dispensing tube to the cartridge. Simultaneously, the cartridge can also be fastened to a carrier in order to form a cartridge system. In this context, the cartridge can be connected to an ampoule.

Moreover, the invention can provide the cartridge to comprise two, three or more feed plungers in one hollow space or in different hollow spaces which, in particular, can be arranged to be parallel to each other.

The object of the invention is also met by a cartridge system for the production of a mixture, preferably a cement, particularly preferably a medical cement, comprising at least one cartridge of this type.

In this context, the invention can provide the cartridge system to comprise an ampoule with a liquid content, in particular a monomer ampoule, and the cartridge to contain a powder, preferably a cement powder.

In this context, the invention can provide the cartridge system to comprise an opening mechanism allowing the ampoule to be opened and the content of the ampoule to be guidable through a tubing into the cartridge, whereby the tubing preferably is connected to the outlet opening of the cartridge.

And lastly, the object of the invention is also met by a method for dispensing a cartridge content, preferably a cement, particularly preferably a medical cement, through the use of a cartridge of this type, preferably through the use of a cartridge system of this type, whereby the feed plunger is unlocked manually before the cartridge content is squeezed out by means of the feed plunger.

In this context, the invention can provide the cartridge content to be mixed with a mixing rod that is guided through the feed plunger before unlocking the feed plunger.

The invention can also provide the cartridge to contain a powder, preferably a cement powder, and a liquid, preferably a monomer liquid, to be guided into the cartridge before unlocking the feed plunger, in particular before mixing the cartridge content.

In this context, it is advantageous to open an ampoule, preferably a monomer ampoule, to provide the liquid.

A refinement of the method according to the invention results from providing gas to be aspirated from the inside of the cartridge through the feed plunger, whereby the liquid preferably is aspirated from the ampoule into the cartridge through the action of a negative pressure on the inside of the cartridge.

In particular for medical purpose, the invention can provide the inside of the cartridge and the cartridge content to be sterilized with a gas, preferably with ethylene oxide.

Manual unlocking of the feed plunger may also be understood to involve the use of simple manually-operated tools. Moreover, aside from the grasping parts, another accessible mechanical device may be provided that converts a manually applied force into the unlocking of the feed plunger.

The invention also proposes a device for mixing and dispensing bone cement that is made up of at least one cement container, one mixing organ, and one vacuum connection. The device possesses a feed plunger that can be shifted in the cement container and possesses at least one snap-in element that projects axially beyond the plane of the outside of the feed plunger. In this context, the cement container is a cylindrical cartridge that is filled with a cement powder.

The invention is also implemented through a device for mixing and dispensing bone cement that comprises at least one cement container (a cartridge), one mixing organ, one feed plunger with at least one sealing element, and one vacuum connection, whereby at least one feed plunger is arranged such that it can be shifted in said cement container, possesses, at the opening pointing towards the end of the powder container, at least one snap-in element (snap-in means) that can be bent or shifted in the direction of the axis or opposite to the axis of the feed plunger, whereby the snap-in element projects axially beyond the plane of the outside of the feed plunger, the snap-in element possesses at least one snap-in device that engages a groove of the cement container or reaches over the edge of the cement container, and whereby the external surface of the snap-in element that is oriented opposite to the axis of the feed plunger has a sufficient size to allow same to be bent or slid manually in the direction of the axis or opposite to the axis of the feed plunger.

In this context, the invention can provide two snap-in elements to preferably be arranged to be opposite from each other. By this means, lightly pressing with an index finger and thumb allows the snap-in elements to be pushed or slid in the direction of the axis of the feed plunger and thus the feed plunger to be unlocked and shifted axially in the cement container (the cartridge).

Moreover, the invention can provide the feed plunger to possess notches in the feed plunger jacket below the snap-in element each in extension of the outsides of the snap-in element. By this means, the snap-in element can be pushed or slid manually more easily in the direction of the axis of the feed plunger using thumb and index finger. The only thing to note in this context is that the notches must end above the sealing elements of the feed plunger.

The object is also met by the use of a cartridge of this type, in particular through the use of a method of this type, for squeezing out pasty one-component polymethylmethacrylate bone cements, pasty two-component polymethylmethacrylate bone cements, pasty three-component polymethylmethacrylate bone cements, dental impression materials, inorganic bone cements and/or polymethylmethacrylate bone cements, preferably through mixing a powder component and a liquid monomer component.

The invention is based on the surprising finding that one or more simple locking devices arranged directly on the feed plunger allows or allow the feed plunger to be fastened to the cartridge wall in a detachable manner. In this context, the structure is particularly easy and inexpensive to implement. A simple hook on the feed plunger to be hooked into the end of the cartridge wall on which the feed plunger is to be positioned fixedly in the starting state is sufficient as a locking device. The snap-in means, i.e., for example, the feet of the hook, are then positioned outside the cartridge wall and are thus easily accessible.

The cartridge is particularly easy to operate if, in addition, grasping parts are arranged on the locking devices that can be used to conveniently detach the snap-in means. In this case, the opposite snap-in device no longer needs to hook into the end of the cartridge wall, but rather can engage a groove or any other opposite snap-in means in the region of the feed plunger, since manual operability is provided through the grasping parts projecting beyond the cartridge wall. The grasping parts or grasping part are/is expediently shaped to be ergonomic in shape in order to facilitate operation by hand or using thumb and index finger. However, a tool or specialized tool may be used just as well for operation of the locking device.

It must be considered to be an essential advantage of the invention that the cartridge wall is not weakened by cut-outs at the sites exposed to the highest loads. A groove that is not arranged on the inside of the cartridge therefore does not weaken the structure, since no negative pressure occurs there upon evacuation of the inside of the cartridge and since no pressure is exerted through the feed plunger upon the cartridge being squeezed out, Cut-outs of this type are predetermined breakage sites for the cartridge and either need to be reinforced with much effort or the cartridge wall must be built-up to be thicker, i.e. using more material.

The invention can also provide that the snap-in device is arranged above or below a plane of the outside of the plunger. This means that the snap-in device, in the form of a snap-in nose below the plane of the outside of the feed plunger, can engage a circumferential groove that is arranged in the internal space of the cartridge. Arranging the snap-in device above the plane of the feed plunger, the snap-in nose can project beyond the edge of the cartridge and thus prevent an axial motion of the feed plunger in the hollow space.

BRIEF DESCRIPTION OF THE SEVERAL VIEWS OF THE DRAWING(S)

Figure 2:
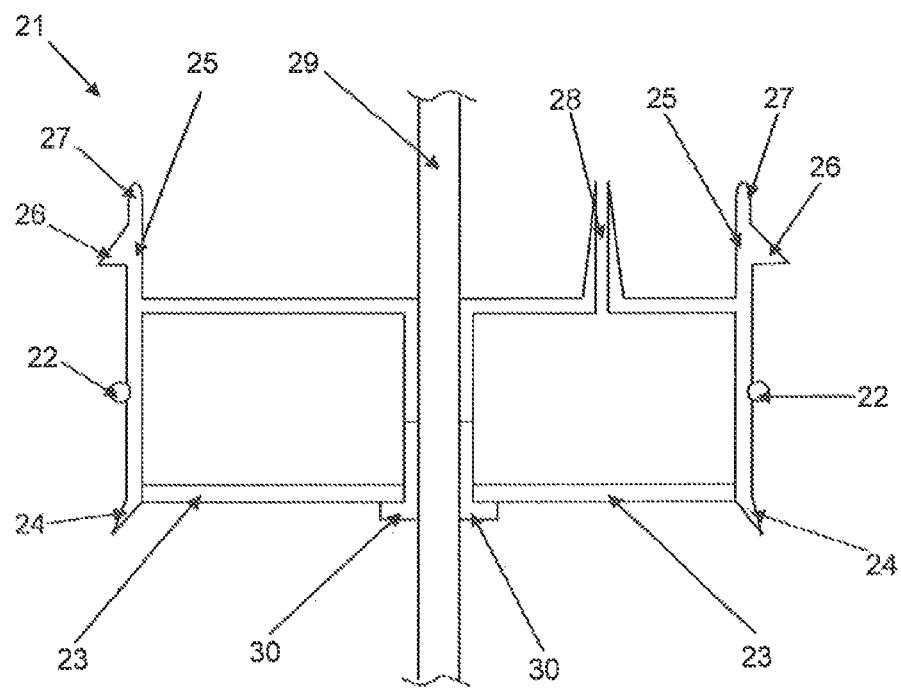
Figure 3:
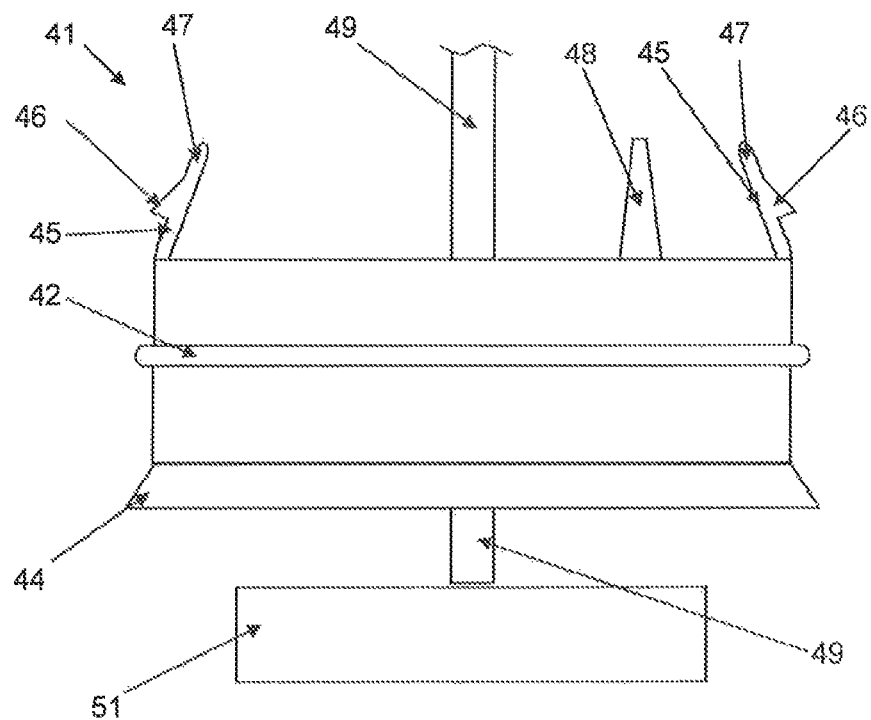
Figure 4:
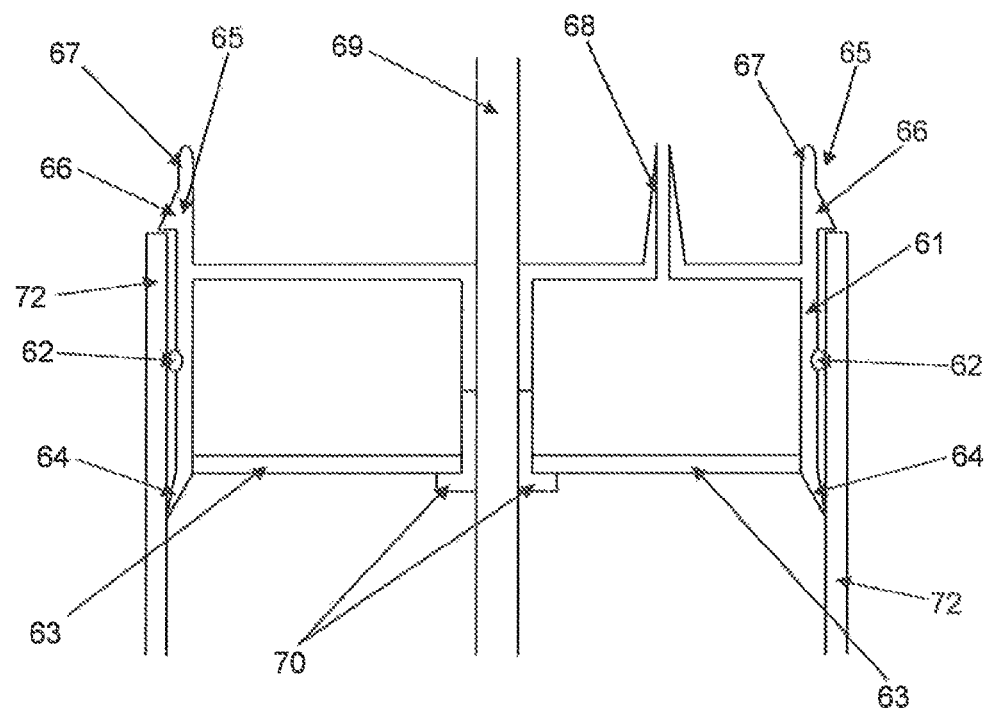
Figure 5:
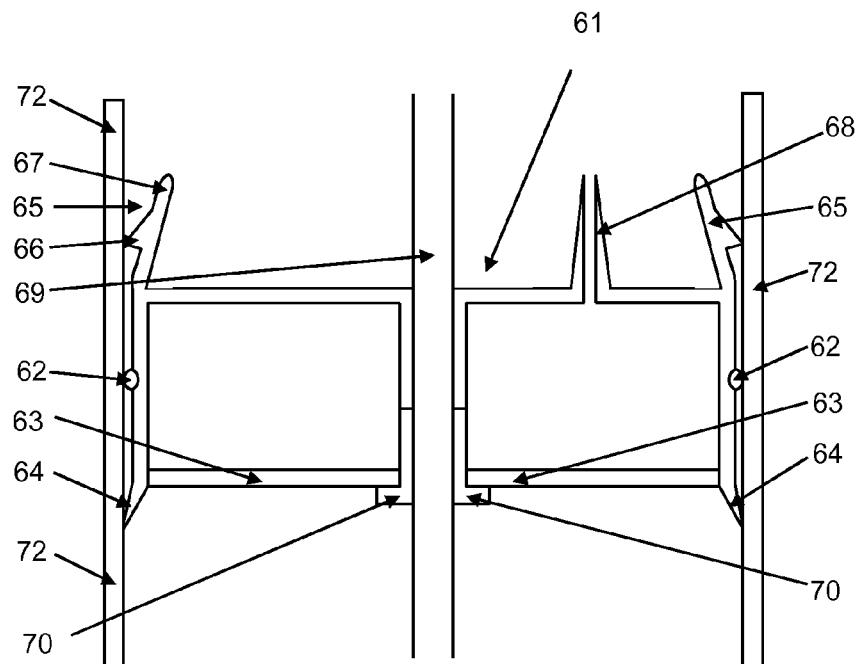
Figure 6:
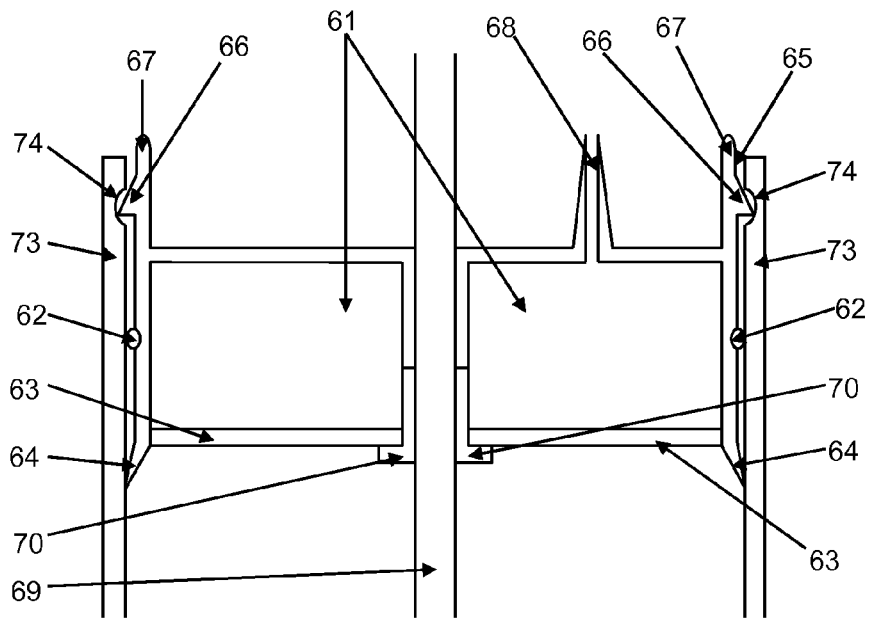
Figure 7:
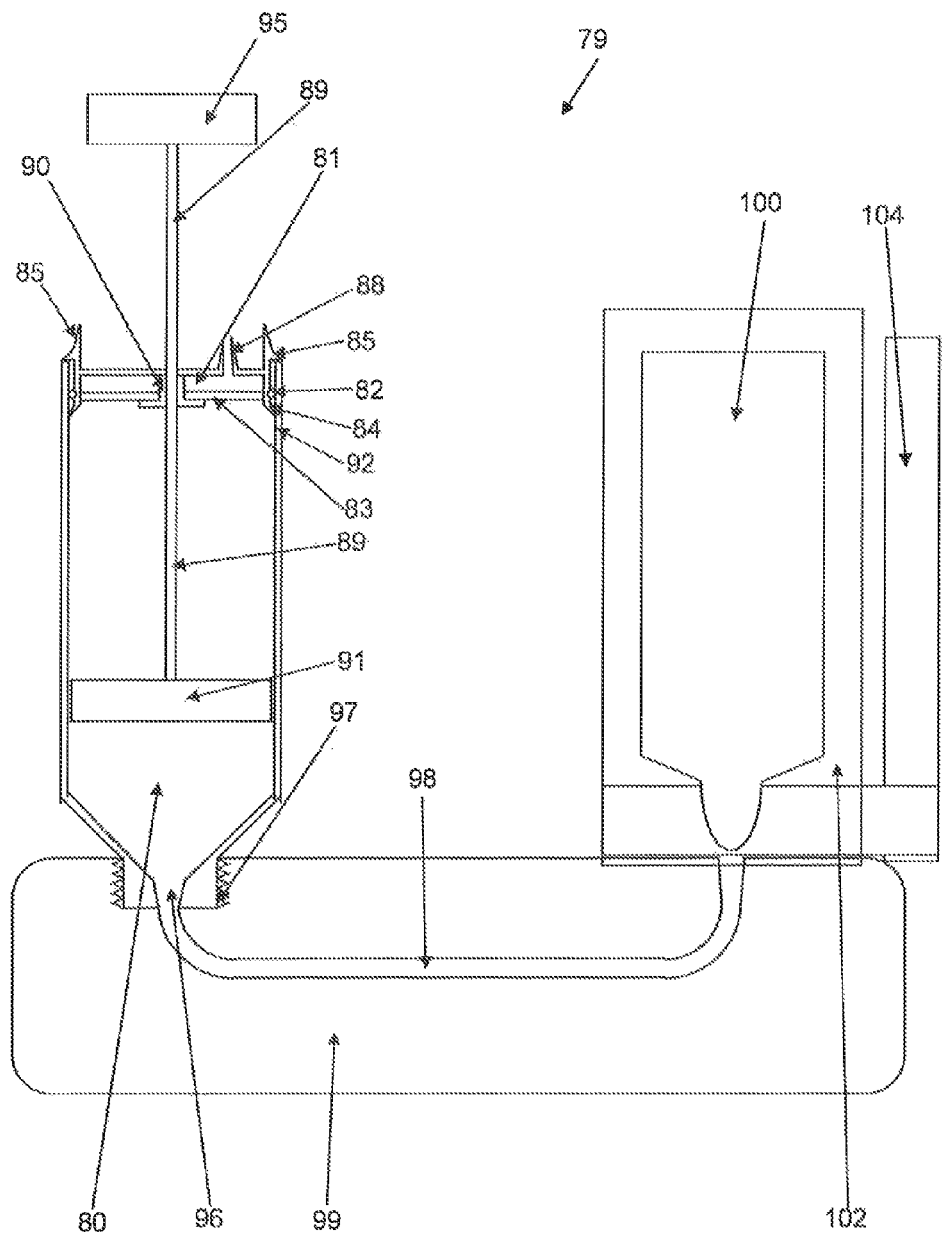

Exemplary embodiments of the invention shall be illustrated in the following on the basis of seven schematic figures, though without limiting the scope of the invention. In the figures:

FIG. 1: shows a schematic cross-sectional view of a feed plunger according to the invention for a cartridge according to the invention, FIG. 2: shows a schematic cross-sectional view of a second feed plunger according to the invention having a bushing for a cartridge according to the invention, FIG. 3: shows a schematic side view of a feed plunger according to the invention having a bushing with the snap-in element being compressed, FIG. 4: shows a schematic cross-sectional view of a region of a cartridge according to the invention with a feed plunger being locked, FIG. 5: shows a schematic cross-sectional view of the cartridge according to the invention with the feed plunger being unlocked and slid-in, FIG. 6: shows a schematic cross-sectional view of a region of a second cartridge according to the invention with locked feed plunger, and FIG. 7: shows a schematic cross-sectional view of a cartridge system according to the invention with a cartridge according to the invention.

DETAILED DESCRIPTION OF THE INVENTION

FIG. 1 shows a schematic cross-sectional view of a feed plunger 1 for a cartridge ac cording to the invention. The cylindrical feed plunger 1 is hollow inside and is made of a simple plastic material, for example through an injection molding procedure. An elastic seal 2, for example made of rubber, is arranged around the circular circumference of the feed plunger 1. The bottom side of the feed plunger 1 is closed through a porous disc 3. Wiping lips 4 are arranged on the lower end of the side walls of the feed plunger 1 and, with the feed plunger 1 being inserted into a cartridge according to the invention, shall prevent the material to be conveyed on the inside of the cartridge to be pressed through laterally between the walls of the feed plunger 1 and the internal walls of the cartridge to the seal 2 upon a motion of the feed plunger 1 on the inside of the cartridge (downwards in FIG. 1). For this purpose, the wiping lips 4 are made of a flexible, elastic material. The elasticity of the wiping lips 4 can also be attained through reducing their thickness to the extent that the desired elasticity results even using the same plastic material of which the remaining feed plunger 1 is made.

Two locking devices 5 are arranged on the upper end of the side walls of the feed plunger 1 and each comprise a snap-in means 6 and a grasping part 7. When the two snap-in devices 5 are compressed in the direction of the cylinder axis, for example through pressing them together by the grasping parts 7 with index finger and thumb, the locking devices tip in the direction of the cylinder axis upon which the snap-in means 6 are tipped also. If the snap-in means 6 previously engaged an opposite snap-in device (not shown) at the cartridge wall or reached over the cartridge wall, the compression detaches the locking of the feed plunger 1 to the cartridge wall.

A vacuum connection 8 through which the inside of the feed plunger 1 can be evacuated is provided on the top of the feed plunger 1. With the feed plunger 1 in its assembled state, this allows the inside of the cartridge that is arranged below the porous disc 3 to be evacuated as well. The porous disc 3 is permeable to gas, but to powders. This allows a gas to be pumped off from the inside of the cartridge through the porous disc 3 or a gas to be guided into the inside of the cartridges while a powder or cement contained on the inside of the cartridge cannot permeate through the porous disc 3.

The vacuum connection 8 and the porous disc 3 are superfluous for the locking function of the feed plunger 1. Accordingly, a cartridge according to the invention is obtained also f, instead of the porous disc 3, simply a single-part, massive feed plunger 1 is manufactured through an injection molding procedure without providing an opening, such as vacuum connection 8. The exclusive purpose of the vacuum connection 8 and porous disc 3 is to enable gas to be exchanged on the inside of the cartridge without allowing a powder stored in the cartridge to exit. This is advantageous in particular in case of a medical application since the cartridge content can then be sterilized through supplying a sterilizing gas, such as ethylene oxide. This also applies to all of the following exemplary embodiments.

FIG. 2: shows a schematic cross-sectional view of an alternative feed plunger 21 for a cartridge according to the invention. Said feed plunger 21 is also structured to be cylindrical. A rubber seal 22 is arranged around the circumference of the feed plunger 21. On its floor side, the feed plunger 21 is closed through a semi-permeable porous disc 23. A wiping lip 24 that surrounds the feed plunger 21 along its entire circumference is arranged in the lower region of the feed plunger 21. Two locking devices 25 are arranged in the upper region of the feed plunger 21. The locking devices 25 each comprise a snap-in means 26 and a grasping part 27 that can be used to operate the locking devices 25.

A vacuum connection 28 through which the feed plunger 21 and, in the assembled state, the cartridge as well (not shown) can be evacuated is arranged on the top of the feed plunger 21. A cylindrical mixing rod 29 is arranged through the feed plunger 21 and is supported in the feed plunger 21 like by a bearing through a bushing. A second seal (not shown) may be arranged in the bushing. A guide sleeve 30 that guides the mixing rod 29, holds the semi-permeable porous disc 23, and seals the feed plunger 21 with respect to the mixing rod 29 is arranged in the lower region of the bushing.

FIG. 3 shows a schematic side view of a feed plunger 41 for a cartridge according to the invention. A rubber seal 42 surrounds the feed plunger 41 along its entire circumference. A flexible wiping lip 44 that also surrounds the feed plunger 41 along its entire circumference is arranged at the lower edge of the feed plunger 41. Locking devices 45 are provided on the upper edge of the feed plunger 41 and can be used to fasten the feed plunger 41 to a cartridge wall (not shown) of the cartridge. The locking devices 45 comprise a snap-in means 46 and a grasping part 47. The locking devices 45 are tilted in the direction of the centre of the feed plunger 41 through a force acting on the grasping parts 47. This also moved the snap-in means 46 in the direction of the centre of the feed plunger 41, whereby the locking of the snap-in means 46 to the cartridge wall is undone. The feed plunger 41 is then freely mobile inside the cartridge.

A vacuum connection 48 is arranged on the top of the feed plunger 41. A rod of a mixing rod 49 is arranged through the centre of the feed plunger 41 such as to be mobile (can be twisted and slid) in the feed plunger 41. A mixing vane 51 that can be used to mix the cartridge content is provided on the bottom side of the mixing rod 49 that is arranged on the inside of the cartridge when the feed plunger 41 is in its assembled state.

FIG. 4 shows a schematic cross-sectional view of a part of a cartridge according to the invention with a locked feed plunger 61. A seal 62 is provided on the feed plunger 61 for sealing the inside of the cartridge on the bottom in FIG. 4). The bottom side of the feed plunger 61 facing the inside of the cartridge is formed by a gas-permeable porous disc 63. The outer edge of the feed plunger 61 is bordered on its bottom side by a circumferential wiping lip 64 designed to prevent material from the inside of the cartridge to be pushed past the feed plunger 61 towards the outside. Two locking devices 65 are arranged outside on the top of the feed plunger 61 and each comprise a snap-in means 66 and a grasping part 67. Moreover, a vacuum connection 68 onto which a hose can be plugged is arranged on the top of the feed plunger 61. A mixing rod 69 is guided through the centre of the feed plunger 61 and sealed and positioned through a guiding sleeve 70. The mixing rod 69 is supported in feed plunger 61 as by a bearing such that it can rotate.

The feed plunger 61 is situated in the upper part of a cartridge having a cylindrical hollow space that is bordered by a cartridge wall 72. The lower surfaces of the snap-in means 66 abut on the upper edge of the cartridge wall 72 and thus prevent the feed plunger 61 from being shiftable into the inside of the cartridge (downwards in FIG. 4). FIG. 4 therefore shows the locked position of the feed plunger 61 in the cartridge.

Even when the inside of the cartridge is being evacuated through the vacuum connection 68, the locked feed plunger 61 cannot be pulled into the inside of the cartridges. The locking also prevents the feed plunger 61 from moving when the mixing rod 69 is in use.

In order to detach the feed plunger 61, the grasping parts 67 of the locking device 65 simply need to be pushed in the direction of the mixing rod 69 either manually or through the aid of a simple tool. If the cartridge is intended for single use, the locking devices 65 can also be deformed reversibly or irreversibly or even broken off in order to unlock the feed plunger 61.

FIG. 5 shows a schematic cross-sectional view of the same structure according to FIG. 4 with the feed plunger 61 being unlocked. The locking devices 65 are bent inwards such that the snap-in means 66 no longer engage the upper edge of the cartridge wall 72. Owing to a pressure that acts on the top of the feed plunger 61 and is caused by evacuation of the inside of the cartridge and/or a mechanical force acting from above on the feed plunger 61, the feed plunger 61 has been shifted into the inside of the cartridge (downwards in FIG. 5). In this context, the wiping lips 64 prevent material that is being pressed downwards through the moving feed plunger 61 to become situated between the external wall of the feed plunger 61 and the cartridge wall 72.

FIG. 6 shows an alternative schematic structure of a cartridge according to the invention in a cross-sectional view with the same feed plunger 61 as according to FIGS. 4 and 5. In contrast to FIGS. 4 and 5, the cartridge wall 73 according to FIG. 6 has grooves 74 provided in it that serve as opposite snap-in means for the snap-in means 66 of the locking devices 65. The grasping parts 67 of the locking devices 65 are sufficiently long to project beyond the upper edge of the cartridge wall 73 and thus from the cylindrical hollow space that is bordered by the cartridge wall 73. The grasping parts 67 and thus the locking device 65 therefore remain manually accessible.

Compressing the grasping parts 67 causes the snap-in means 66 to slip out of the grooves 74 and thus release the feed plunger 61. Subsequently, the feed plunger 61 is mobile in the cylindrical hollow space. The rubber seal 62 abuts on the cartridge wall 73 along the entire circumference of the feed plunger 61 in a gas-tight and pressure-tight manner. This allows a negative pressure to be generated on the inside of the cartridge (on the bottom in FIG. 6) without gas being able to penetrate between the feed plunger and the cartridge wall into the inside of the cartridge.

An outlet opening (not shown) is arranged on the side of the cartridge that is opposite from the feed plunger 61 (with reference to FIG. 6, this is on the bottom and outside of the picture) by means of which the cartridge content can be squeezed from the cartridge by means of the feed plunger 61 after the feed plunger 61 has been unlocked.

FIG. 7 shows a schematic cross-sectional view of the structure of a cartridge system 79 according to the invention having a cartridge 80 according to the invention. A locked feed plunger 81 is arranged in the cartridge 80 and is arranged such as to be mobile on the inside of the cartridge 80 in the longitudinal direction of the cartridge 80 in its unlocked state. The feed plunger 81 comprises a seal 82 and a wiping lip 84 that surround the feed plunger 81 along its entire circumference. Two locking devices 85 are arranged on the feed plunger 81 on the top of the feed plunger 81. A vacuum connection 88 through which the inside of the cartridge 80 can be evacuated is provided on the top of the feed plunger 81.

A mixing rod 89 extends through a guiding sleeve 90 through the feed plunger 81. A mixing vane 91 is arranged on the mixing rod 89 on the inside of the cartridge 80. The mixing rod 89 is supported in the feed plunger 81 as by a bearing in a manner such that it can rotate such that the mixing vane 91 can be rotated in the cartridge 80. The inside of the cartridge 80 is bordered by a cylindrical cartridge wall 92 such that a cylindrical hollow space is formed on the inside of the cartridge 80, which, aside from the lower funnel-shaped part of the internal space (in the lower region of the internal cartridge space in FIG. 7) forms the inside of the cartridge 80.

A grasp 95 is arranged on the upper end of the mixing rod 89 and can be used to operate the mixing rod 89 manually or, just as well, through a motor. On the side of the cartridge 80 that is opposite to the locked feed plunger 81, the internal cartridge space ends in an outlet opening 96 through which a material contained in the cartridge 80 can be squeezed out through the unlocked feed plunger 81. in the region of the outlet open ing 96, the cartridge 80 has an external thread 97 for connecting the cartridge 80 to a tubing 98 of a carrier 99. For this purpose, the cartridge 80 is screwed into an internal thread of the carrier 99.

An ampoule 100 containing a monomer liquid in a container 102 is arranged on the other side of the carrier 99. The ampoule 100 can be opened through an opening mechanism 104 that shears off the head of the ampoule 100.

The cartridge 80 is filled to approx. ⅔ level with a bone cement powder. For sterilization of the content, the inside of the cartridge 80 is initially evacuated through the vacuum connection 88. Subsequently, a sterilizing gas, such as, for example, ethylene oxide, is guided into the cartridge 80. After sufficient time for sterilization of the content of cartridge 80 has elapsed, the ethylene oxide is removed again with a pump.

The opening mechanism 104 is then used to open the ampoule 100 and the monomer liquid flows into the tubing 98. Owing to the negative pressure on the inside of the cartridge 80, the monomer liquid is aspirated into the cartridge 80 where it mixes with the cement powder. The mixing rod 89 and the mixing vane 91 can be used to mix the monomer liquid and the cement powder. Owing to the vacuum, no unwanted air inclusions are generated in the cement mixture that is being produced. After mixing, the feed plunger 81 is being manually unlocked at the locking devices 85. Since the pressure inside the cartridge 80 is lower than in its surroundings, the feed plunger 81 is pulled into the inside of the cartridge 80. The cartridge 80 is opened on its front, for example by operating a valve (not shown), or the cartridge 80 is unscrewed from the carrier 99. Pushing the feed plunger 81 in then causes the cement mixture to be squeezed out of the inside of the feed plunger 81 through the outlet opening 96.

A dispensing tube can be screwed onto the thread 97 such that the bone cement can easily be applied at the desired site.

The features of the invention disclosed in the preceding description and in the claims, figures, and exemplary embodiments, can be essential for the implementation of the various embodiments of the invention both alone and in any combination.

LIST OF REFERENCE NUMBERS 1, 21, 41, 61, 81 Feed plunger
2, 22, 42, 62, 82. Seal
3, 23, 63, 63 Porous disc
4, 24, 44, 64, 84 Wiping lip
5, 25, 45, 65, 85 Locking device
6, 26, 46, 66 Snap-in means
7, 27, 47, 67 Grasping part
8, 28, 48, 68, 88 Vacuum connection
29, 49, 69, 89 Mixing rod 30, 70, 90 Guide sleeve
51, 91 Mixing vane
72, 73, 92 Cartridge wall
74 Groove
79 Cartridge system
80 Cartridge
95 Grasp
96 Outlet opening
97 Thread
98 Tubing
99 Carrier
100 Ampoule
102 Container
104 Opening mechanism

The invention claimed is:

1. A cartridge for squeezing-out a cartridge content, comprising:
   at least one cylindrical hollow space bordered by a cartridge wall,
   at least one feed plunger that is movably arranged in a hollow space along the cylinder axis of the hollow space and abuts on the cartridge wall,
   at least one snap-in means for selectively locking the feed plunger in place at the cartridge wall,
   at least one locking device arranged on the feed plunger which comprises at least one of the snap-in means, the at least one locking device is accessible from outside when the feed plunger is locked,
   wherein the feed plunger comprises a cylindrical bushing,
   further comprising a mixing rod arranged in the bushing and projects from the hollow space for mixing a cartridge content in the hollow space, and which comprises a pre-determined breakage site.

2. The cartridge according to claim 1, further comprising a mixing vane, arranged on the mixing rod on the inside of the cartridge.

3. A cartridge for squeezing-out a cartridge content, comprising:
   at least one cylindrical hollow space bordered by a cartridge wall,
   at least one feed plunger that is movably arranged in a hollow space along the cylinder axis of the hollow space and abuts on the cartridge wall,
   at least one snap-in means for selectively locking the feed plunger in place at the cartridge wall,
   at least one locking device arranged on the feed plunger which comprises at least one of the snap-in means, the at least one locking device is accessible from outside when the feed plunger is locked,
   wherein the feed plunger comprises a vacuum connection through which gas is evacuatable from the inside of the cartridge, wherein at least one semi-permeable wall, is arranged in the gas bushing of the vacuum connection which is permeable to gas and impermeable to powder.

4. The cartridge according to claim 3, wherein each locking device comprises at least one grasping part,
   the at least one grasping part projects at least partially, from the hollow space, such that the locking device is unlockable manually and/or is arranged on the inside of a part of the hollow space that is accessible from outside such that each locking device is unlockable manually from outside through the at least one grasping part.

5. The cartridge according to claim 3, wherein the at least one locking device is connected to the feed plunger in a fixed manner.

6. The cartridge according to claim 5, wherein the at least one locking device is connected to the feed plunger in that the at least one locking device and the feed plunger form one part.

7. The cartridge according to claim 3, wherein the at least one locking device comprises two locking devices provided on the feed plunger and are situated opposite to each other.

8. The cartridge according to claim 3, wherein cartridge wall includes an edge and wherein the at least one snap-in means reach over the edge of the cartridge wall and/or into a groove in the cartridge wall, wherein the groove is arranged in a region of the cartridge wall over which the part of the feed plunger abutting on the cartridge wall does not travel while the cartridge is being squeezed out.

9. The cartridge according to claim 3, wherein at least one locking device is shiftable, tipped and/or bent in direction of the cylinder axis of the hollow space or breakable off of the feed plunger.

10. The cartridge according to claim 9, wherein the at least one locking device is broken off the feed plunger by manual means.

11. The cartridge according to claim 3, wherein the snap-in means, at least partially, project over the edge of the cartridge wall in radial direction with respect to the cylinder axis of the hollow space when the feed plunger is locked.

12. The cartridge according to claim 3, wherein the hollow space is closed on one side through the feed plunger or is separated into a region on the inside of the cartridge and a region that is accessible from outside.

13. The cartridge according to claim 3, wherein the feed plunger comprises at least one sealing ring which abuts circumferentially the cartridge wall.

14. The cartridge according to claim 3, wherein the feed plunger comprises, below the at least one snap-in means, at least one notch in the feed plunger each notch in extension of outsides of the at least one snap-in means.

15. The cartridge according to claim 3, wherein the cartridge comprises an outlet opening in a form of a dispensing tube for dispensing the cartridge content, on a side opposite from the feed plunger in the locked position.

16. The cartridge according to claim 15, further comprising a fastening means arranged in a region of the outlet opening of the cartridge.

17. The cartridge according to claim 16, wherein the fastening means is a thread.

18. The cartridge according to claim 17, wherein the thread is an external thread.

19. The cartridge according to claim 3, wherein the cement is medical cement.

20. The cartridge according to claim 3, wherein the at least one semi-permeable wall is a porous disc.

21. A cartridge system for producing medical cement, comprising:
    a cartridge for squeezing-out a cartridge content, including
    at least one cylindrical hollow space bordered by a cartridge wall,
    at least one feed plunger that is movably arranged in a hollow space along a cylinder axis of the hollow space and abuts on the cartridge wall,
    at least one snap-in means for selectively locking the feed plunger in place at the cartridge wall,
    at least one locking device arranged on the feed plunger and comprises at least one of the snap-in means which is accessible from outside when the feed plunger is locked,
    wherein the cartridge system comprises an ampoule with a liquid content, and the cartridge contains a cement powder.

22. The cartridge system according to claim 21, wherein the cartridge system comprises an opening mechanism, allowing the ampoule to be opened and the content of the ampoule is guided through a tubing into the cartridge.

23. The cartridge system according to claim 22, wherein the tubing is connected to the outlet opening of the cartridge.

24. A method for dispensing a cartridge content, comprising the steps of:
- providing a cartridge including at least one cylindrical hollow space bordered by a cartridge wall,
- providing at least one feed plunger movably arranged in a hollow space along the cylinder axis of the hollow space and abuts on the cartridge wall,
- providing at least one snap-in means for selectively locking the feed plunger in place at the cartridge wall,
- providing at least one locking device arranged on the feed plunger and including at least one of the snap-in means which is accessible from outside when the feed plunger is locked,
- wherein the feed plunger is being unlocked manually before the cartridge content is squeezed out by means of the feed plunger,
- wherein the cartridge content is mixed with a mixing rod which is guided through the feed plunger before unlocking the feed plunger.

25. A method for dispensing a cartridge content, comprising the steps of:
- providing a cartridge including at least one cylindrical hollow space bordered by a cartridge wall,
- providing at least one feed plunger movably arranged in a hollow space along the cylinder axis of the hollow space and abuts on the cartridge wall,
- providing at least one snap-in means for selectively locking the feed plunger in place at the cartridge wall,
- providing at least one locking device arranged on the feed plunger and including at least one of the snap-in means which is accessible from outside when the feed plunger is locked,
- wherein the feed plunger is being unlocked manually before the cartridge content is squeezed out by means of the feed plunger,
- wherein the cartridge contains a cement powder and a liquid, guided into the cartridge before unlocking the feed plunger and before mixing the cartridge content,
- wherein the liquid is contained in an ampoule, and is opened to provide the liquid.

26. The method according to claim 25, wherein the ampoule is a monomer ampoule.

27. A method for dispensing a cartridge content, comprising the steps of:
- providing a cartridge including at least one cylindrical hollow space bordered by a cartridge wall,
- providing at least one feed plunger movably arranged in a hollow space along the cylinder axis of the hollow space and abuts on the cartridge wall,
- providing at least one snap-in means for selectively locking the feed plunger in place at the cartridge wall,
- providing at least one locking device arranged on the feed plunger and including at least one of the snap-in means which is accessible from outside when the feed plunger is locked,
- wherein the feed plunger is being unlocked manually before the cartridge content is squeezed out by means of the feed plunger,
- further comprising the step of aspirating gas from the inside of the cartridge through the feed plunger.

28. The method according to claim 27, wherein the liquid is aspirated from the ampoule into the cartridge by applying a negative pressure on the inside of the cartridge.

29. A method for dispensing a cartridge content, comprising the steps of:
- providing a cartridge including at least one cylindrical hollow space bordered by a cartridge wall,
- providing at least one feed plunger movably arranged in a hollow space along the cylinder axis of the hollow space and abuts on the cartridge wall,
- providing at least one snap-in means for selectively locking the feed plunger in place at the cartridge wall,
- providing at least one locking device arranged on the feed plunger and including at least one of the snap-in means which is accessible from outside when the feed plunger is locked,
- wherein the feed plunger is being unlocked manually before the cartridge content is squeezed out by means of the feed plunger,
- wherein the cartridge and the cartridge content are sterilized with a gas.

30. The method according to claim 29, wherein the cartridge is sterilized with ethylene oxide.

* * * * *